(12) United States Patent
Boyle et al.

(10) Patent No.: US 10,301,340 B2
(45) Date of Patent: May 28, 2019

(54) NICKEL METAL NANOPARTICLE SYNTHESIS

(71) Applicant: National Technology & Engineering Solutions of Sandia, LLC, Albuquerque, NM (US)

(72) Inventors: Timothy J. Boyle, Albuquerque, NM (US); LaRico Juan Treadwell, Albuquerque, NM (US)

(73) Assignee: National Technology & Engineering Solutions of Sandia, LLC, Albuquerque, NM (US)

( * ) Notice: Subject to any disclaimer, the term of this patent is extended or adjusted under 35 U.S.C. 154(b) by 147 days.

(21) Appl. No.: 15/668,208

(22) Filed: Aug. 3, 2017

(65) Prior Publication Data

US 2018/0051046 A1 Feb. 22, 2018

Related U.S. Application Data

(60) Provisional application No. 62/378,092, filed on Aug. 22, 2016.

(51) Int. Cl.
| | | |
|---|---|---|
| *C07F 15/04* | (2006.01) | |
| *B22F 9/24* | (2006.01) | |
| *B22F 1/00* | (2006.01) | |
| *C22B 3/00* | (2006.01) | |
| *B82Y 40/00* | (2011.01) | |
| *B82Y 30/00* | (2011.01) | |

(52) U.S. Cl.
CPC .......... *C07F 15/045* (2013.01); *B22F 1/0018* (2013.01); *B22F 9/24* (2013.01); *C22B 23/0461* (2013.01); *B82Y 30/00* (2013.01); *B82Y 40/00* (2013.01); *Y10S 977/773* (2013.01); *Y10S 977/81* (2013.01); *Y10S 977/896* (2013.01)

(58) Field of Classification Search
None
See application file for complete search history.

(56) References Cited

U.S. PATENT DOCUMENTS

| | | | |
|---|---|---|---|
| 2005/0245701 A1* | 11/2005 | Oshima | C08F 10/00 526/160 |
| 2013/0066029 A1* | 3/2013 | Radlauer | C07F 15/04 526/171 |
| 2015/0125177 A1* | 5/2015 | Yu | B05D 1/24 399/101 |

OTHER PUBLICATIONS

Campora, J. et al., "Synthesis and Structure of Three Unusual Homoleptic Aryloxides of Nickel and Palladium", Organometallics, vol. 21, pp. 1014-1016, published Feb. 12, 2002.*
Zuideveld, M.A. et al., "Remote Substituents Controlling Catalytic Polymerization by Very Active and Robust Neutral Nickel(II) Complexes", Angewandte Chemie International Edition, vol. 43, pp. 869-873, published 2004.*
Lipschutz, M.I. et al., "Useful Method for the Preparation of Low-Coordinate Nickel(I) Complexes via Transformations of the Ni(I) Bis (amido) Complex K{Ni[N(SiMe3)(2,6-iPr2—C6H3)]2}", Organometallics, vol. 33, pp. 5566-5570, published Aug. 22, 2014.*

(Continued)

*Primary Examiner* — George Wyszomierski
(74) *Attorney, Agent, or Firm* — Kevin W. Bieg

(57) ABSTRACT

Nickel nanoparticles can be synthesized using a variety of precursors (e.g., nickel amides [Ni(NR$_2$)$_2$], alkyls [NR$_2$], and alkoxides [Ni(OR)$_2$]).

13 Claims, 12 Drawing Sheets

(56) References Cited

OTHER PUBLICATIONS

Gerung, H. et al., "Solution Synthesis of Germanium Nanowires Using a Ge2+ Alkoxide Precursor", J. Am. Chem. Soc., 2006, pp. 5244-5250, vol. 128.
Boyle, T. J. et al., "Synthesis, Characterization, and Electrochemical Properties of a Series of Sterically Varied Iron(II) Alkoxide Precursors and Their Resultant Nanoparticles", Inorganic Chemistry, 2011, pp. 6174-6182, vol. 50.
Boyle, T. J. et al., "Precursor Structural Influences on the Final ZnO Nanoparticle Morphology from a Novel Family of Structurally Characterized Zinc Alkoxy Alkyl Precursors", Chem. Mater., 2004, pp. 3279-3288, vol. 16.
Boyle, T. J. et al. "Structural Variations of Potassium Aryloxides", Inorganic Chemistry, 2003, pp. 5357-5366, vol. 42.
Boyle, T. J. et al., "Cadmium Amido Alkoxide and Alkoxide Precursors for the Synthesis of Nanocrystalline CdE (E=S, Se, Te)", Inorganic Chemistry, 2005, pp. 1309-1318, vol. 44.
Boyle, T. J. et al., "Advances in Structurally Characterized Lanthanide Alkoxide Aryloxide, and Silyloxide Compounds", Chemical Reviews, 2008, pp. 1896-1917, vol. 108.
Boyle, T. J. et al., "Synthesis and Characterization of a Family of Solvated Sodium Aryloxide Compounds", Inorganica Chimica Acta, 2013, pp. 374-386, vol. 405.
Boyle, T. J. et al., "Structural Diversity in Solvated Lithium Aryloxides. Syntheses, Characterization, and Structures of [Li(OAr)(THF)x]n and [Li(OAr)(py)x]2 Complexes Where OAr=OC6H5, OC6H4(2-Me), OC6H3(2,6-(Me))2, OC6H4(2-Pri), OC6H3(2,6-(Pri))2, OC6H4(2-But), OC6H3(2,6-(But))2", Inorganic Chemistry, 2000, pp. 5133-5146, vol. 39.
Bunge, S. D. et al., "Synthesis of Coinage-Metal Nanoparticles from Mesityl Precursors", Nano Letters, 2003, pp. 901-905, vol. 3.

\* cited by examiner

NICKEL METAL NANOPARTICLE SYNTHESIS

CROSS-REFERENCE TO RELATED APPLICATION

This application claims the benefit of U.S. Provisional Application No. 62/378,092, filed Aug. 22, 2016, which is incorporated herein by reference.

STATEMENT OF GOVERNMENT INTEREST

This invention was made with Government support under Contract No. DE-NA0003525 awarded by the United States Department of Energy/National Nuclear Security Administration. The Government has certain rights in the invention.

FIELD OF THE INVENTION

The present invention relates to nickel nanoparticle synthesis using a variety of precursors (e.g., nickel amides [Ni(NR$_2$)$_2$], alkyls [NR$_2$], and alkoxides [Ni(OR)$_2$]).

BACKGROUND OF THE INVENTION

The physical properties (phase, size, morphology) of nickel metal nanoparticles (Ni-NPs) can have a dramatic impact on their properties. Ni-NPs have been isolated in either the face-centered cubic (fcc) or metastable hexagonal closed packed (hcp) structure, which reportedly alters their magnetic properties: fcc Ni-NPs have exhibited ~30 times stronger M-H data compared to the hcp Ni-NPs. See M. Richard-Plouet et al., *Chem. Mater.* 19, 865 (2007); M. Han et al., *Adv. Mater.* 19, 1096 (2007); C. N. Chinnasamy et al., *J. Appl. Phys.* 97, 10J309 (2005); and J. Gong et al., *J. Alloys Compd.* 457, 6 (2008). Additionally, the size of the Ni—NP imparts different final properties: 15 nm Ni-NPs are superparamagnetic with magnetic saturation 2% less than bulk Ni$^0$, whereas 20 nm and larger Ni-NPs are ferromagnetic. See S. Carenco et al., *Chem. Mater.* 22, 1340 (2010); and B. Tanushree et al., *Nanotechnology* 20, 415603 (2009). Morphology also plays a role in the final properties, with cube-shaped Ni-NPs reportedly demonstrating 10 times more magnetic saturation than spherical nanoparticles of the same size. See A. P. LaGrow et al., *J. Am. Chem. Soc.* 134, 855 (2012). Therefore, controlling the crystalline phase, size, and morphology is critical in order to tailor the final properties of Ni-NPs.

Several synthetic routes are available for the production of Ni-NPs, including pyrolysis, sputtering, reversed micelles, and aqueous/non-aqueous chemical reduction routes. See Y. He et al., *Chem. Mater.* 17, 1017 (2005); G. Ausanio et al., *Appl. Phys. Lett.* 85, 4103 (2004); G. B. Thompson et al., *Acta Mater.* 50, 643 (2002); D.-H. Chen and S.-H. Wu, *Chem. Mater.* 12, 1354 (2000); M. Han et al., *Adv. Mater.* 19, 1096 (2007); L. Yonghua et al., *Nanotechnology* 17, 1797 (2006); N. Cordente et al., *Nano Lett.* 1, 565 (2001); and Y. Chen et al., *J. Nanosci. Nanotechnol.* 9, 5157 (2009). The majority of these research efforts have focused on altering the Ni—NP properties by varying the surfactant and monomer concentration. The precursors used are often commercially available (i.e., halides, acetates, and nitrates), with particular attention paid to nickel acetylacetonate for the production of spherical and cube Ni-NPs. See M. Green and P. O'Brien, *Chem. Commun.* (Cambridge, U. K.), 1912 (2001); Y. Hou and S. Gao, *J. Mater. Chem.* 13, 1510 (2003); M. L. Singla et al., *Appl. Catal., A* 323, 51 (2007); S.-H. Wu and D.-H. Chen, *J. Colloid Interface Sci.* 259, 282 (2003); L. Chen et al., *Mater. Sci. Eng., A* 452-453, 262 (2007); A. Wang et al., *Catal. Commun.* 10, 2060 (2009); K. J. Carroll et al., *J. Phys. Chem. C* 115, 2656 (2011); S. Mourdikoudis et al., *J. Magn. Magn. Mater.* 321, 2723 (2009); J. Gong et al., *J. Alloys Compd.* 457, 6 (2008); V. Tzitzios et al., *Nanotechnology* 17, 3750 (2006); S. Carenco et al., *Chem. Mater.* 22, 1340 (2010); A. P. LaGrow et al., *J. Am. Chem. Soc.* 134, 855 (2012); Y. Chen et al., *J. Nanosci. Nanotechnol.* 9, 5157 (2009); O. Pascu et al., *Langmuir* 26, 12548 (2010); and C. Yuanzhi et al., *Nanotechnology* 18, 505703 (2007). Some efforts have explored the use of tailored precursors such as nickel 1,5-cyclooctadiene or oleate which generate Ni$^0$ nanorods (~12-17 nm) or petal-like nanomaterials (15-20 nm), respectively. See N. Cordente et al., *Nano Lett.* 1, 565 (2001); and M. Han et al., *Adv. Mater.* 19, 1096 (2007).

However, a need remains for precursors that have utility in the generation of nickel metal nanoparticles.

SUMMARY OF THE INVENTION

The present invention is directed to the synthesis of novel precursors such as [Ni(NR$_2$)$_2$], [NiCp$_2$], and Ni(OR)$_2$ and their utility in generating Ni-NPs. [Ni(NR$_2$)$_2$] can be synthesized from NiBr$_2$ and two equivalents of KNR$_2$ (R—Si (CH$_3$)$_3$) in THF at 0° C. NiCp$_2$ can be synthesized by reacting NiCl$_2$ with two equivalents of NaCp (Cp=C$_5$H$_5$) in THF at 0° C. Ni(OR)$_2$ can be synthesized using an amide-alcohol exchange reaction using nickel amide [Ni(NR$_2$)$_2$] and an alcohol (ROH). For example, a novel family of nickel(II) aryloxide ([Ni(OAr)$_2$(py)$_x$]) can be synthesized from an amide-alcohol exchange using [Ni(NR$_2$)$_2$] and an alkyl phenol [H—OAr] in the presence of pyridine (py). The H—OAr can be a mono- or di-ortho-substituted alkyl phenol. For example, the alkyl phenol can be alkyl=methyl (H-oMP), isopropyl (H-oPP), tert-butyl (H-oBP)) or a 2,6 dialkyl phenol (alkyl=di-iso-propyl (H-DIP), di-t-butyl (H-DBP), di-phenyl (H-DPhP)). The crystalline nickel(II) aryloxide products are solvated monomers and structurally characterized as [Ni(OAr)$_2$(py)$_x$], where x=4: OAr=oMP, oPP; x=3: OAr=oBP, DIP; or x=2: OAr=DBP, DPhP. The nickel(II) aryloxides, as well as [Ni(NR$_2$)$_2$] and [NiCp$_2$], can be decomposed under solution precipitation routes to form irregular shape nickel metal nanoparticles (e.g., 8-15 nm) with different crystalline phases such as fcc, hcp, or fcc and hcp, respectively.

BRIEF DESCRIPTION OF THE DRAWINGS

The detailed description will refer to the following drawings, wherein like elements are referred to by like numbers.

DETAILED DESCRIPTION OF THE INVENTION

Figure 1:
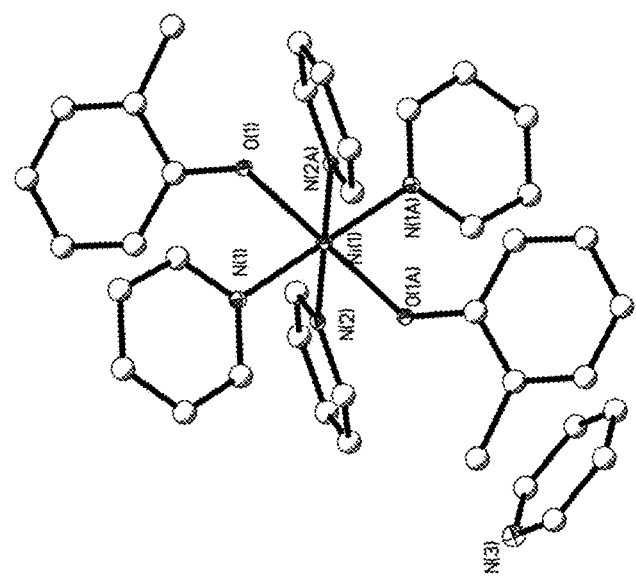
FIG. 1 is a structure plot of [Ni(oMP)$_2$(py)$_4$] (compound 1). Thermal ellipsoids of heavy atoms are drawn at the 30% level and carbon atoms are represented by ball and stick diagrams for clarity.
Figure 2:
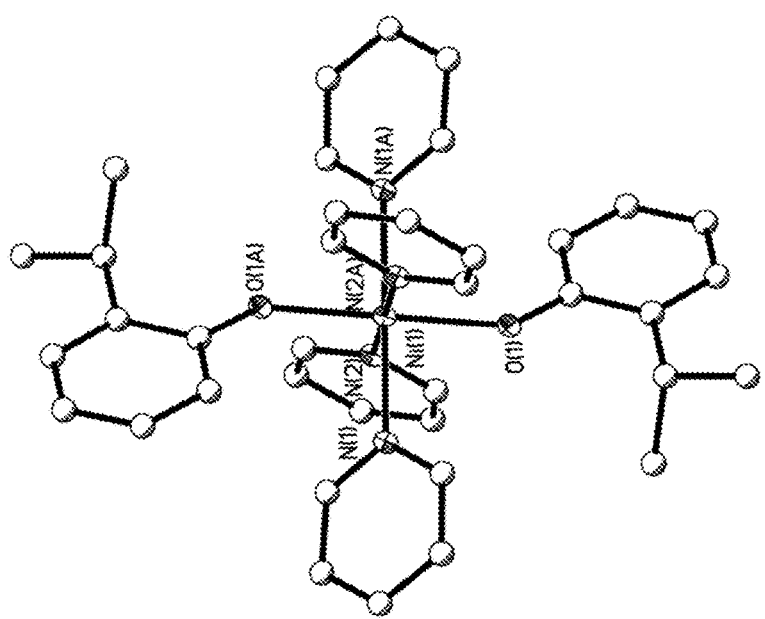
FIG. 2 is a structure plot of [Ni(oPP)$_2$(py)$_4$] (compound 2). Thermal ellipsoids of heavy atoms are drawn at the 30% level and carbon atoms are represented by ball and stick diagrams for clarity.
Figure 3:
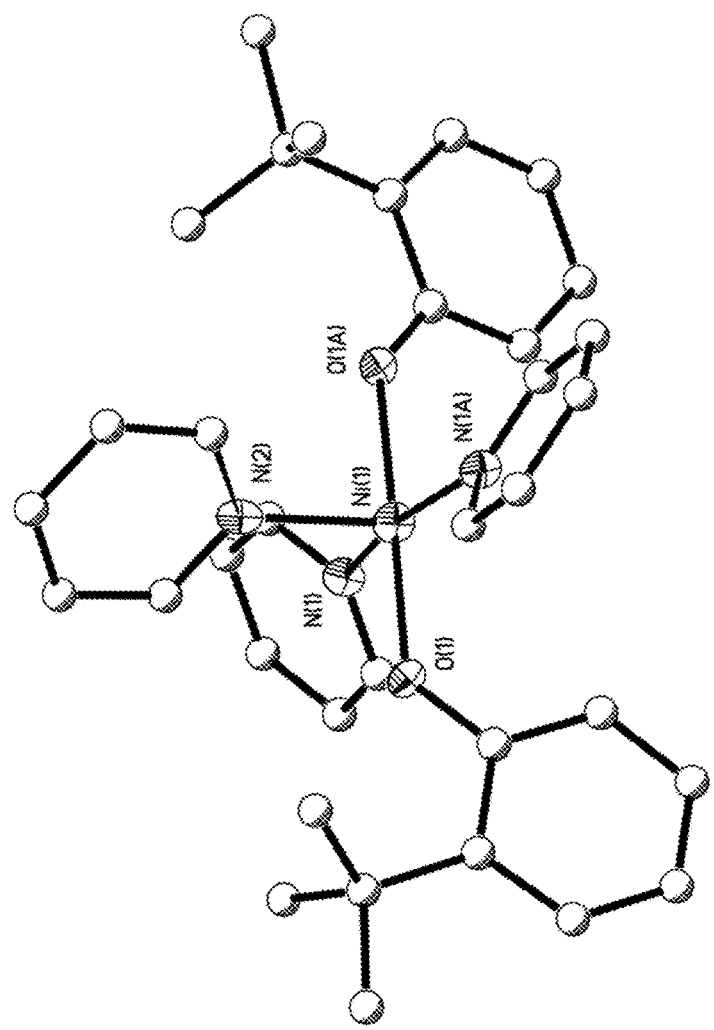
FIG. 3 is a structure plot of [Ni(oBP)$_2$(py)$_3$] (compound 3). Thermal ellipsoids of heavy atoms are drawn at the 30% level and carbon atoms are represented by ball and stick diagrams for clarity.
Figure 4:
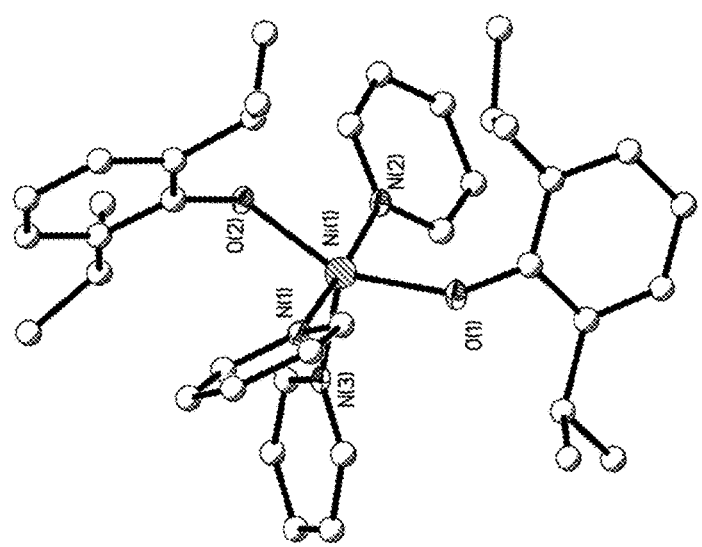
FIG. 4 is a structure plot of [Ni(DIP)$_2$(py)$_3$] (compound 4). Thermal ellipsoids of heavy atoms are drawn at the 30% level and carbon atoms are represented by ball and stick diagrams for clarity.
Figure 5:
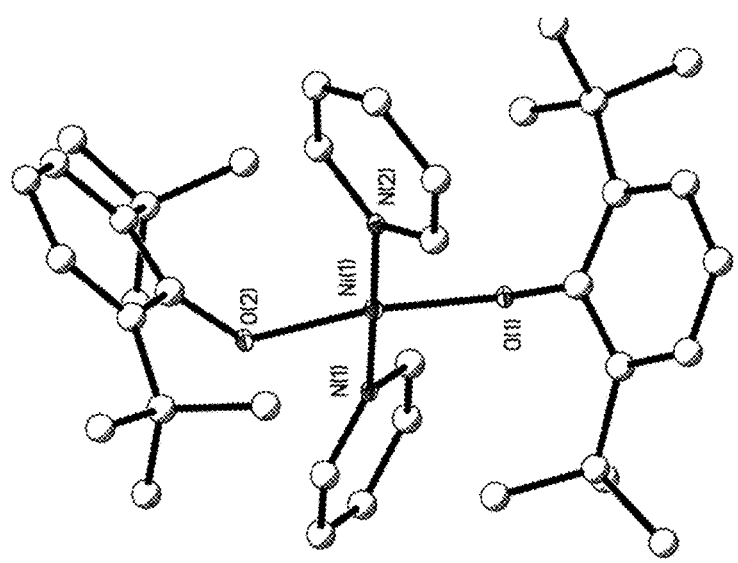
FIG. 5 is a structure plot of [Ni(DBP)$_2$(py)$_2$] (compound 5). Thermal ellipsoids of heavy atoms are drawn at the 30% level and carbon atoms are represented by ball and stick diagrams for clarity.
Figure 6:
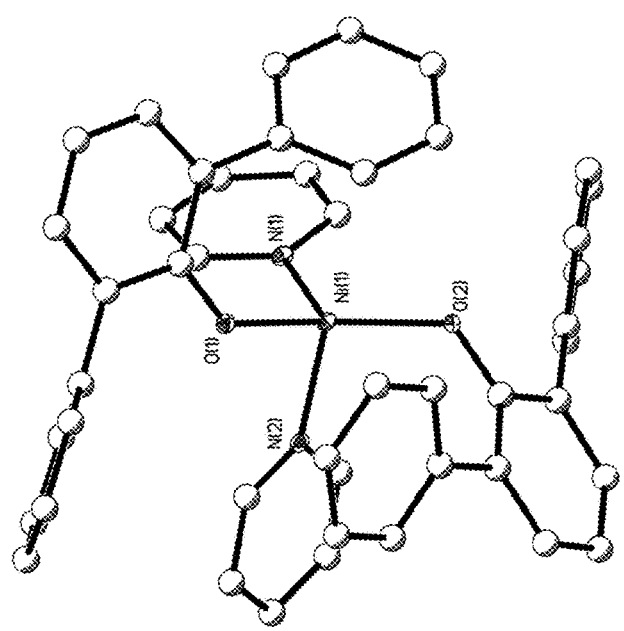
FIG. 6 is a structure plot of [Ni(DPhP)$_2$(py)$_2$] (compound 6). Thermal ellipsoids of heavy atoms are drawn at the 30% level and carbon atoms are represented by ball and stick diagrams for clarity.

Due to their widespread applicability, nickel metal nanoparticles (Ni-NPs) have garnered tremendous attention. These nanoparticles are typically synthesized from commercially available precursors. However, there is little precedent on the utility of tailored precursors such as nickel amides [Ni(NR$_2$)$_2$], alkyls [NiR$_2$], and alkoxides ([Ni(OR)$_x$]) to generate Ni-NPs. The limited investigation of ([Ni(OR)$_x$]) may be due to the limited number of 'simple' [Ni(OR)$_x$] compounds that have been previously structurally characterized and disseminated. See R. Adams et al., *Aust. J. Chem.* 19, 207 (1966). The utility of [M(OR)$_x$] precursors to produce metal nanoparticles (M-NP) and MO$_x$ has been well documented. See H. Gerung et al., *J. Am. Chem. Soc.* 128, 5244 (2006); T. J. Boyle et al., *Inorg. Chem.* 50, 6174 (2011); T. J. Boyle et al., *Chem. Mater.* 16, 3279 (2004); and T. J. Boyle et al., *Inorg. Chem.* 42, 5357 (2003). The interest in the [M(OR)$_x$] precursors stems from their high solubility, low decomposition temperature, and ease of ligand modification. The luxury of manipulation of these compounds has allowed investigation of the "precursor structure affect" to control the morphology in numerous nanoceramic systems and determine how the nuclearity and coordination impact the final properties of the NPs generated. See T. J. Boyle et al., *Chem. Mater.* 16, 3279 (2004); and T. J. Boyle et al., *Inorg. Chem.* 44, 1309 (2005). Therefore, the present invention is directed to the synthesize of nickel alkoxides [Ni(OR)$_x$], nickel amides [Ni(NR$_2$)$_2$], and nickel alkyls [NiCp$_2$] and their utility in the generation of Ni-NPs.

The synthesis of [Ni(NR$_2$)$_2$] followed literature preparation of [M(NR$_2$)], with slight modification. NiBr$_2$ (10 g, 46 mmols) was slowly added to a stirring solution of KNR$_2$ (R=Si(CH$_3$)$_3$) (18.26 g, 91.5 mmol) in tetrahydrofuran (THF). The reaction was stirred for 12 h, filtered, and dried. The final product yielded a dark red oil, which crystalized at low temperatures. However, no single crystal X-ray data could be obtained due to the instability of the crystals at room temperature. Elemental analysis was collected on the bulk sample and was consistent with the calculated values. For the alkyl precursor synthesis, NiCp$_2$, two equivalents NaCp were added to a stirring solution of NiCl$_2$ in THF at 0° C. The reaction was stirred for 12 h, filtered, and dried. The bulk green product was dissolved in toluene, where crystals formed after slow evaporation of the solvent. FTIR and elemental analysis was obtained on the bulk product, while single crystal X-ray diffraction was conducted on isolated crystals. The crystal structure of NiCp$_2$ consists of two cyclopentadienyl rings bound on opposition sides of the nickel atoms, which is commonly referred to as a sandwich compound.

According to the present invention, [Ni(OR)$_x$] compounds were synthesized from the reaction of bis[bis(trimethylsilyl)amido]nickel(II) [Ni(NR$_2$)$_2$](R=SiMe$_3$) with two equivalents of an alkyl phenol (alkyl=methyl (H-oMP), isopropyl (H-oPP), tert-butyl (H-oBP)) or a 2,6 dialkyl phenol (alkyl=di-isopropyl (H-DIP), di-butyl (H-DBP), di-phenyl (H-DPhP)) as shown in equation 1:

(1)
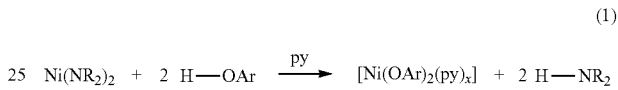
$$Ni(NR_2)_2 + 2\ H\text{—}OAr \xrightarrow{py} [Ni(OAr)_2(py)_x] + 2\ H\text{—}NR_2$$

where OAr=oMP (compound 1), oPP (compound 2), oBP (compound 3), DIP (compound 4), DBP (compound 5), or DPhP (compound 6). As will be described below, all products were characterized by single crystal X-ray diffraction, which yielded monomers: [Ni(OAr)$_2$(py)$_x$], where py=pyridine; and x=4: OAr=oMP, oPP; x=3: OAr=oBP, DMP, DIP; or x=2: OAr=DBP, DPhP. Selected compounds from this new family of [Ni(OAr)$_2$] precursors were used to generate nanoparticles via a solution precipitation (SPPT) route, employing hexadecylamine (HDA) and octylamine (ON). The details of the synthesis and characterization of [Ni(OAr)$_2$], their utility in generating Ni-NPs, and the characterization of the Ni-NPs are described below.

All syntheses were performed under conditions precluding exposure to atmospheric oxygen and moisture using standard Schlenk line and argon filled glovebox techniques. All solvents were received in sealed bottles and stored under argon atmosphere, including pyridine (py), toluene (tol), and methanol (MeOH). The following chemicals were used as received: [KNR$_2$] where R=Si(Me$_3$), NiBr$_2$, NaCp (Cp=C$_5$H$_5$), H-oMP, H-oPP, H-oBP, H-DIP, H-DBP, and H-DPhP. [Ni(NR$_2$)$_2$] was synthesized according to literature routes from the reaction of NiBr$_2$ with two equivalents of KNR$_2$ in THF at 0° C. See H. Gerung et al., *J. Am. Chem. Soc.* 128, 5244 (2006); and T. J. Boyle et al., *Chem. Rev.* (Washington, D.C., U.S.) 108, 1896 (2008). The [Ni(NR$_2$)$_2$] was then reacted with a series of ortho-substituted phenols. See T. J. Boyle et al., *Inorg. Chem.* 42, 5357 (2003); and T. J. Boyle et al., *Inorg. Chim. Acta* 405, 374 (2013). In an argon-filled glovebox, a clear solution of a stoichiometric mixture of H—OAr dissolved in py was added to a vial containing a dark black mixture of [Ni(NR$_2$)$_2$] also dissolved in py. After stirring for 12 h, the solution was set aside with the vial uncapped until crystals formed by slow evaporation. A fraction of the crystals was isolated for single crystal X-ray diffraction, while the rest of the materials were dried either to a green (compounds 1-5) or an orange/reddish (compound 6) powder for bulk analysis. An FTIR spectrum was obtained for each dried sample and the loss of the HO— stretch around 3000 cm$^{-1}$ was used as an indication of completeness of the reaction. For each of the OAr investigated, the representative stretches and bends were observed along with a Ni—O stretch at ν(Ni—O) at ~1600 and 420 cm$^{-1}$. This is consistent with the ν(Ni—O) reported for Ni—O bearing complexes. See D. C. Bradley et al., *Metal Alkoxides*; Academic Press INC., (1978); and R. Li et al., *Scientific Reports* 6, 18737 (2016). Yields were not optimized.

[Ni(oMP)$_2$(py)$_4$] (compound 1) was synthesized using NiNR$_2$ (0.500 g, 1.31 mmol), H-oMP (0.285 g, 2.64 mmol), and py. The yield was 78.9% (0.502 g).

[Ni(oPP)$_2$(py)$_4$] (compound 2) was synthesized using NiNR$_2$ (0.500 g, 1.31 mmol), H-oPP (0.361 g, 2.64 mmol), and py. The yield was 35.5% (0.302 g).

[Ni(oBP)$_2$(py)$_3$] (compound 3) was synthesized using NiNR$_2$ (0.500 g, 1.31 mmol), H-oBP (0.401 g, 2.64 mmol), and py.

[Ni(DIP)$_2$(py)$_3$] (compound 4) was synthesized using NiNR$_2$ (0.500 g, 1.31 mmol), H-DIP (0.471 g, 2.64 mmol), and py. The yield was 74.5% (0.632 g).

[Ni(DBP)$_2$(py)$_2$] (compound 5) was synthesized using NiNR$_2$ (0.500 g, 1.31 mmol), H-DBP (0.545 g, 2.64 mmol), and py. The yield was 72.3% (0.593 g).

[Ni(DPhP)$_2$(py)$_2$] (compound 6) was synthesized using NiNR$_2$ (0.500 g, 1.31 mmol), H-DPhP (0.653 g, 2.64 mmol), and py. The yield was 75% (0.691 g).

The isolated crystals were structurally characterized by single-crystal X-ray diffraction. General X-ray crystal structure information for compounds 1-6 are given in Table 1. The crystal structures of compounds 1-6 are shown in FIGS. 1-6, respectively. The products were all solved as monomers with the Ni adopting a variety of geometries due to the degree of solvation as dictated by the steric hindrance of the ortho-substituent. For compounds 1 and 2, the Ni-centers were solved in a distorted-octahedral geometry (CN-6) through two axial trans OAr ligands and four equatorial py solvent molecules. The Ni metal centers of compounds 3-4 were solved in a square base pyramidal geometry (CN-5) with a py solvent occupying the apical position, two trans OAr ligands, and two py molecules in the basal plane. Compound 5 was solved as a distorted square planar (CN-4) monomeric Ni metal center with the two trans OAr ligands and two trans py solvent molecules. For compound 6, the increased steric bulk of the ortho-substituent phenyl ligand forces the coordination of solvent molecules and forces a CN-4 tetrahedral (T-4) geometry Elemental analyses of compounds 1-6 were attempted. Numerous attempts to find meaningful values that were in agreement between the single crystal values and the experimental data were undertaken. The analyses appear to be in good agreement with the crystal structures observed for the majority of samples and preferential ligands loss (i.e. solvent) for the remaining samples. See T. J. Boyle et al., *Inorg. Chem.* 39, 5133 (2000); and T. J. Boyle et al., *Inorg. Chim. Acta* 405, 374 (2013).

Figure 7:
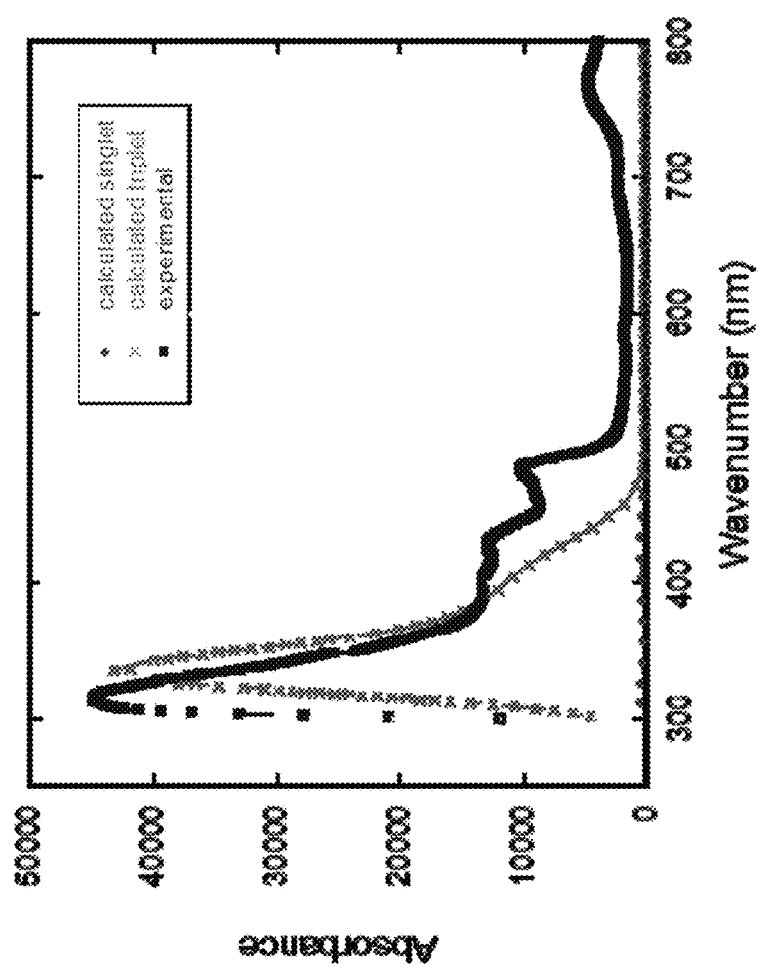
FIG. 7 is a graph of the UV-vis spectra for compound 1 (calculated singlet; x calculated triplet, experimental).

Further attempts were undertaken to characterize the bulk materials using UV-vis spectroscopy. Each sample was individually dried, dissolved in pyridine, transferred to a UV-cell under an argon atmosphere, and the response measured in the visible region (300-800 nm). Due to the limited reports of UV-vis analysis on [Ni(OR)$_2$], computational studies were used to assist in the interpretation of the various electronic transition (singlet or triplet) states and to verify the geometry around the Ni metal center. For all spectra, there is a shift and deviation in the overall intensities between the experimental and calculated spectra. The experimental spectrum of compound 1, shown in FIG. 7, exhibited a strong absorption band at 315 nm and weaker bands at 426 and 486 nm. This curve is mainly consistent with the calculated excitation of the triplet state, which confirms that compound 1 adopts a CN-6 geometry; however, two weaker bands were noted in all of the experimental data that were not present in the calculated spectra. This suggests that some of the starting materials [Ni(NR$_2$)$_2$] may be present as a minor impurity. Nonetheless, the experimental UV-vis spectra match with their corresponding excitation (singlet or triplet) based on the crystal structure observed Ni coordination geometry, such as CN-6 (triplet), CN-5 (singlet), and CN-4 (tetrahedral triplet). As far as compound 6 (CN-4 (square; singlet)) is concerned, it was hard to determine the excitation due to the similarities in the calculated singlet and triplet spectra.

Figure 8:
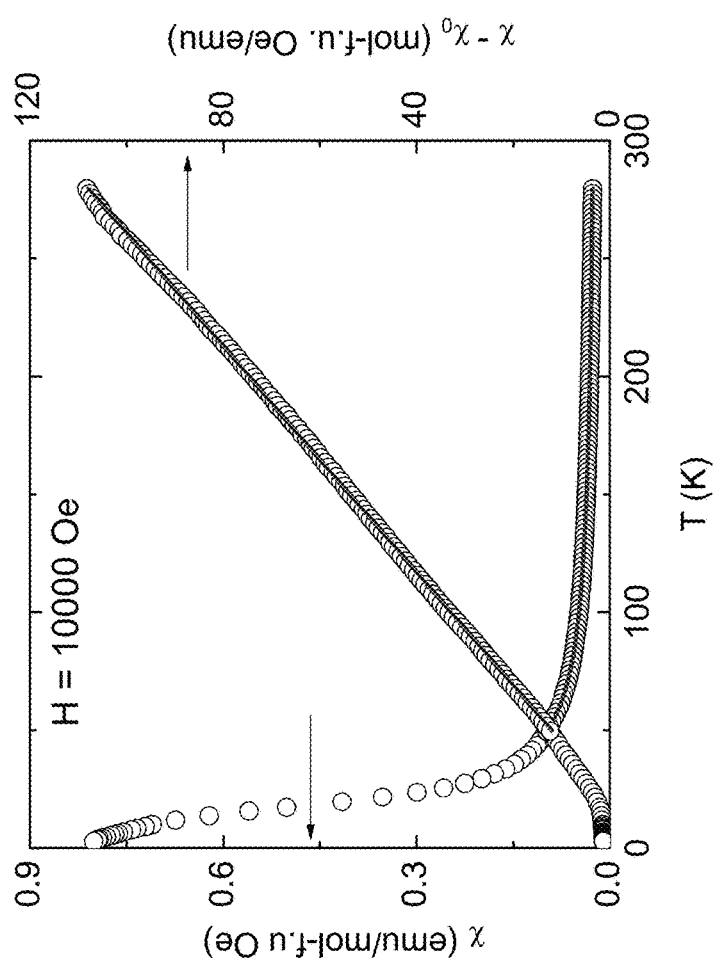
FIG. 8 is a plot of magnetization vs temperature of compound 4 measured at 1 T.

Since these are the first [Ni(OAr)$_2$(py)$_x$] species observed, it was of interest to determine the magnetic susceptibility, the inverse magnetic susceptibility versus temperature, and the magnetization versus field at varying temperatures of these species. Compound 4 was used as a representative sample to identify the oxidation state of nickel center and the behavior of these materials. The results are plotted in FIGS. 8 and 9, respectively. The susceptibility and inverse susceptibility from 50 to 280 K data were fitted with Curie-Weiss models and found to be in good agreement. The Weiss constant was determined to be 21(1) K. This in good agreement with the 17 K maximum found in the -(dM/dT)$_H$ vs. temperature curve (not shown) and suggests that the magnetic interactions between Ni-species are ferromagnetic. The overall fit of the paramagnetic moment was determined to be 4.38(3) $\mu_B$ which is between the calculated spin-only (2.83$\mu_B$) and spin-orbital (5.59$\mu_B$) values for bare Ni$^{2+}$ and the empirical accepted value of 3.2$\mu_B$ for Ni$^{2+}$ containing materials. Such large moments for similar divalent Ni-containing materials have been reported and attributed to high-spin crystal field configurations. See R. Adams et al., *Aust. J. Chem.* 19, 207 (1966).

Figure 9:
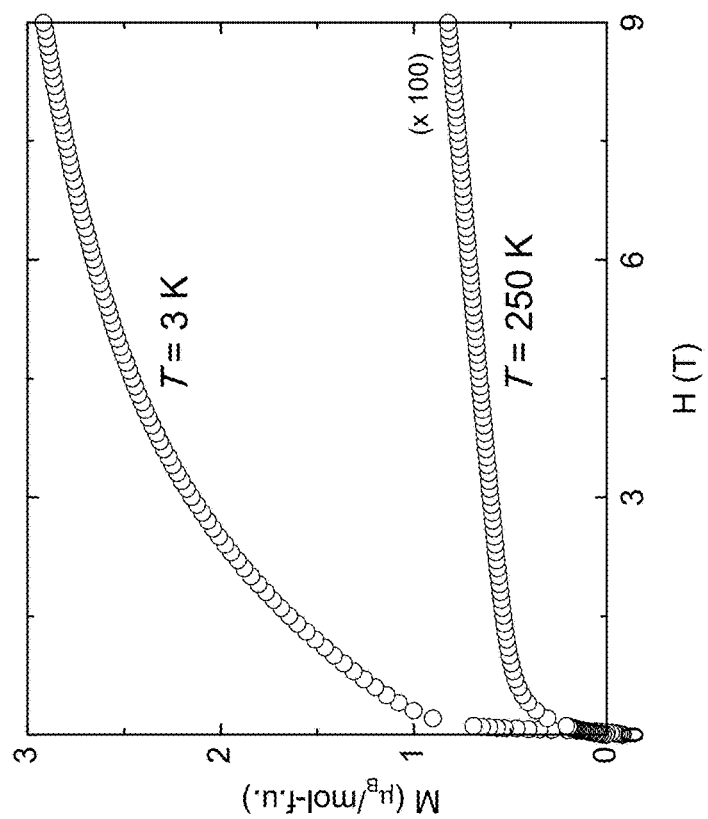
FIG. 9 is a plot of magnetization vs field of compound 4 measured at 250 and 3 K.
Figure 10A:
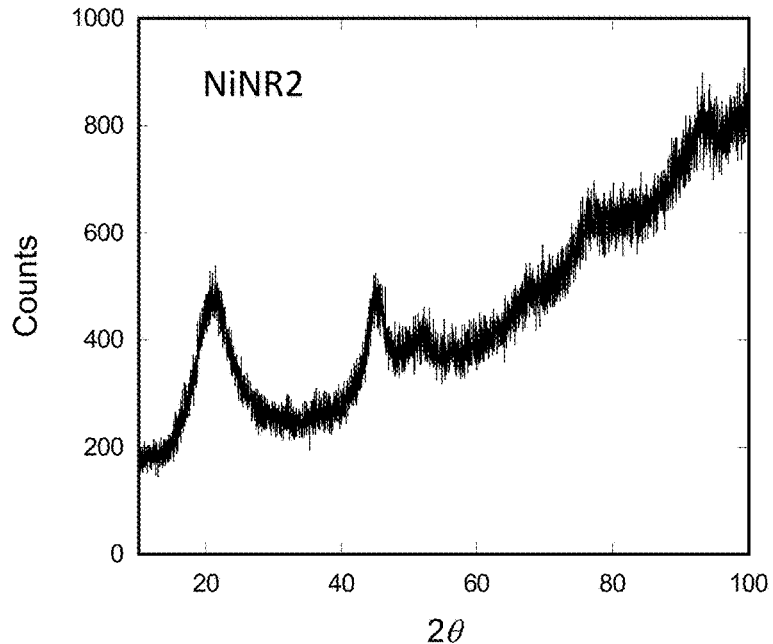
FIG. 10a is a graph of the powder X-ray diffraction (PXRD) pattern of the fcc Ni produced by the decomposition of [Ni(NR$_2$)$_2$].
Figure 10B:
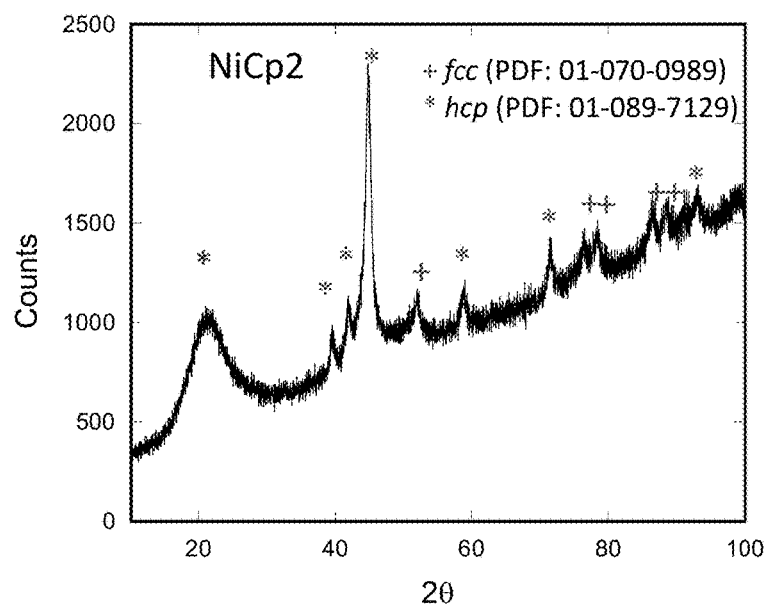
FIG. 10b is a graph of the PXRD pattern of the fcc and hcp Ni produced by the decomposition of NiCp$_2$.
Figure 10C:
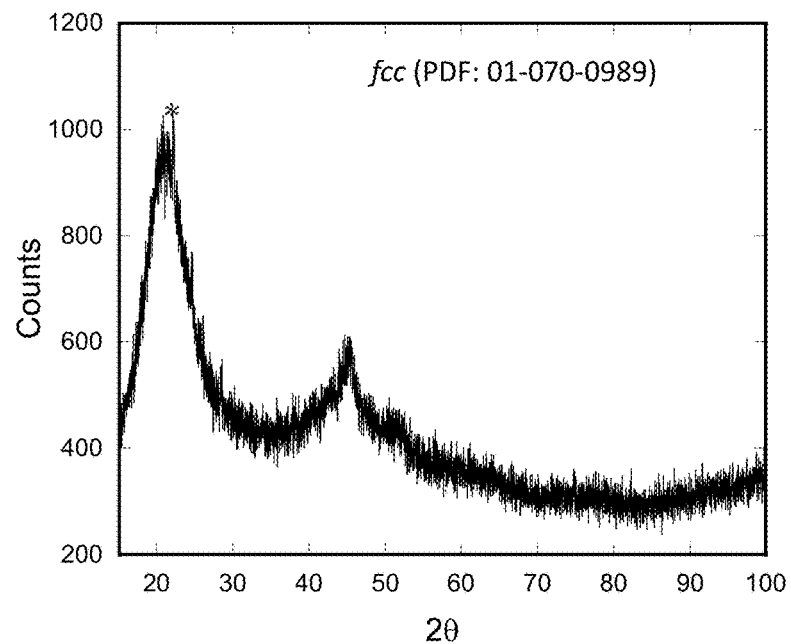
FIG. 10c is a graph of the PXRD pattern of the hcp Ni produced by the decomposition of compound 1.
Figure 10D:
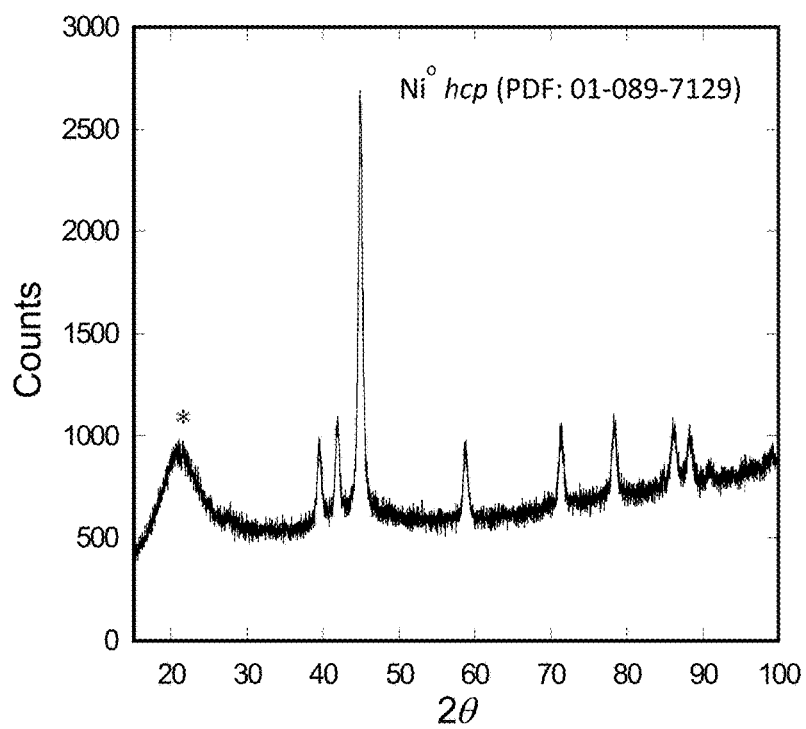
FIG. 10d is a graph of the PXRD pattern of the fcc Ni produced by the decomposition of compound 6.

The magnetization versus field data at 3 K, shown in FIG. 9, exhibit a deviation in the slope between 0 to 0.2 T and subsequently continues to rise to at value of 2.91 $\mu_B$/mol-f.u. at 9 T. The shape of the curve along with the scale of the determined Weiss constant is consistent with soft ferromagnetic order at 3 K. The magnitude of the 250 K magnetization versus field data is greatly reduced relative to that of 3 K data indicating paramagnetic behavior at high temperatures; however, at 250 K and in low fields the magnetization curve shows similar behavior. This has been interpreted as a result of ferromagnetic interaction being dominant at low field at low and high temperature, which is corroborated by the values obtained from the fit (50 K to 280 K) of the susceptibility versus temperature data collected at 1 T with the Curie Models.

Nanoparticle Synthesis

Ni-NPs were generated from this novel family of [Ni(OAr)$_2$(py)$_x$] precursors, as well as [Ni(NR$_2$)$_2$] and [NiCp$_2$].

above description is merely illustrative of the applications of the principles of the present invention, the scope of which is to be determined by the claims viewed in light of the specification. Other variants and modifications of the invention will be apparent to those of skill in the art.

TABLE 1

Data collection parameters for compounds 1-6

| Compound | 1 | 2 | 3 | 4 | 5 | 6 |
|---|---|---|---|---|---|---|
| chemical formula | C$_{34}$H$_{34}$NiN$_6$O$_2$ | C$_{38}$H$_{42}$NiN$_4$O$_2$ | C$_{38}$H$_{42}$NiN$_4$O$_2$ | C$_{39}$H$_{49}$NiN$_3$O$_2$ | C$_{38}$H$_{52}$NiN$_2$O$_2$ | C$_{46}$H$_{36}$NiN$_2$O$_2$ |
| formula weight | 747.54 | 645.45 | 594.40 | 650.52 | 627.52 | 707.48 |
| temp (K) | 173 (2) | 173 (2) | 173 (2) | 173 (2) | 173 (2) | 173 (2) |
| space group | Triclinic, P-1 | Monoclinic, P21/c | Monoclinic, C2/c | Monoclinic, P21/c | Monoclinic, P21/c | Monoclinic, P21/c |
| a (Å) | 10.0616 (14) | 9.5179 (5) | 12.6799 (16) | 18.117 (3) | 14.5737 (6) | 11.6216 (6) |
| b (Å) | 10.6290 (15) | 146472 (8) | 13.4323 (16) | 12.5038 (17) | 10.2425 (4) | 15.5037 (10) |
| c (Å) | 10.9455 (16) | 15.7614 (8) | 19.632 (2) | 17.872 (3) | 22.9227 (9) | 19.9185 (12) |
| α (deg) | 78.105 (6) | | | | | |
| β (deg) | 64.315 (5) | 105.031 (2) | 98.808 (7) | 116.367 (6) | 99.204 (2) | 92.902 (2) |
| γ (deg) | 64.238 (5) | | | | | |
| V (Å$^3$) | 949.8 (2) | 2122.13 (19) | 3304.3 (7) | 3627.4 (9) | 3377.6 (2) | 3584.3 |
| Z | 1 | 2 | 4 | 4 | 4 | 4 |
| D$_{calcd}$(Mg/m$^3$) | 1.307 | 1.010 | 1.195 | 1.191 | 1.234 | 1.311 |
| μ, (Mo, Kα) (mm$^{-1}$) | 0.557 | 0.488 | 0.620 | 0.570 | 0.609 | 0.583 |
| R1$^a$ (%) (all data) | 3.06 | 4.26 | 7.69 | 5.28 | 4.57 | 3.78 |
| wR2$^b$ (all data) | 6.45 | 11.84 | 22.04 | 14.85 | 7.48 | 9.51 |

$^a$R1 = Σ | |F$_o$| − |F$_c$| |/Σ |F$_o$| × 100
$^b$wR2 = [Σ w (F$_o^2$ − F$_c^2$)$^2$/Σ (w |F$_o$|$^2$)$^2$]$^{1/2}$ × 100

Since all the [Ni(OAr)$_2$(py)$_x$] are monomers, compounds 1 and 6 were chosen to represent the 'extreme' (x=6 and 4) geometries available. A SPPT employing ON and HDA was chosen for the preparation of Ni-NPs, although high boiling amine solvents can also be used. See S. D. Bunge et al., Nano Lett. 3, 901 (2003). In an argon filled glovebox, a 3 M solution was prepared by dissolving the appropriate precursor in ON. This room temperature mixture (2 mL) was then injected into a stirring solution of HDA (17 mmols) at 300° C. under flowing argon on a Schlenk line. After heating for ~7 mins at ~225° C., the heating mantle was removed. Upon cooling, the HDA solidified and the reaction was placed under vacuum and transferred into a glovebox. Tol (~15 mL) was added to the solid mixture, yielding a black dispersion. MeOH (~15 mL) was added and the mixture was centrifuged. The supernatant was decanted from the precipitate and washed 3 more times with MeOH (~15 mL).

Figure 11A:
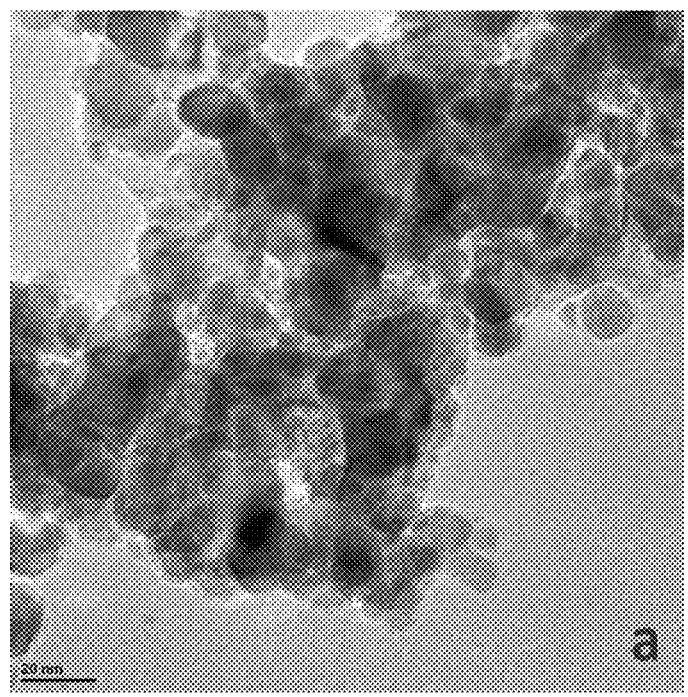
FIG. 11a is a transmission electron micrograph (TEM) analysis of nanoparticles generated from compound 1.
Figure 11B:
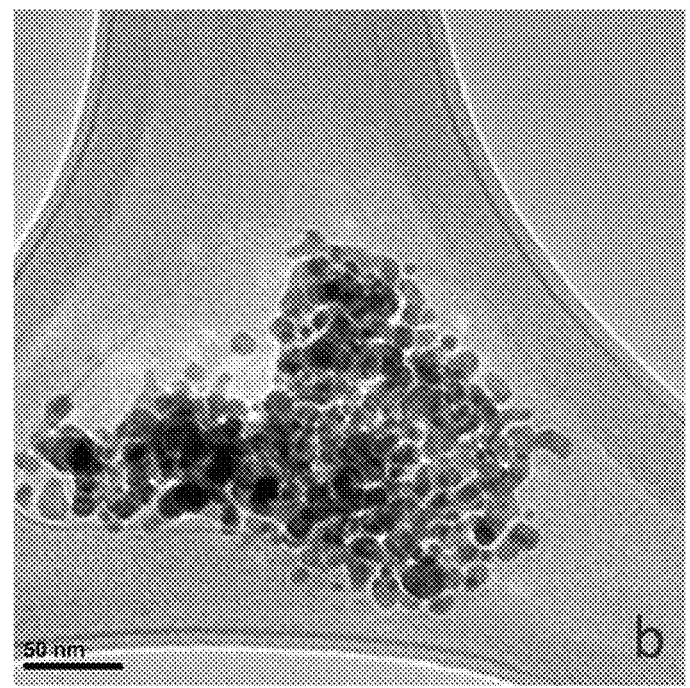
FIG. 11b is a TEM analysis of nanoparticles generated from compound 6.

After working up the reaction, PXRD analyses indicated that the decomposition of [Ni(NR$_2$)$_2$] produced the fcc Ni, [NiCp$_2$] produced the fcc and hcp Ni, compound 1 produced the metastable hcp Ni, and compound 6 produced the fcc Ni. The PXRD patterns of the resultant materials are shown in FIGS. 10a-d, respectively. Based on the sharpness of the PXRD pattern, the nanomaterials obtained from the decomposition of the precursors are very crystalline. In contrast, the resultant product formed from compound 6 yielded broad, weak diffraction peaks. TEM analyses of the black precipitate isolated for [Ni(NR$_2$)$_2$] and [NiCp$_2$]. TEM analysis for compounds 1 and 6 are shown in FIGS. 11a-b. As can be observed, the decomposition of compounds 1 and 6 yielded plate-like morphologies, where the resultant from compound 6 appear to be more oblong in comparison. The particulate size of compound 6 spans a smaller size dispersion than noted for compound 1 based on visual inspection of the TEM pictures.

The present invention has been described as a nickel metal nanoparticle synthesis. It will be understood that the

We claim:

1. A method to synthesize a nickel(II) aryloxide, comprising reacting bis[bis(trimethylsilyl)amido]nickel(II) with an alkyl phenol to form a nickel(II) aryloxide according to the reaction:

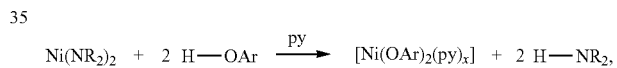

Ni(NR$_2$)$_2$ + 2 H—OAr $\xrightarrow{py}$ [Ni(OAr)$_2$(py)$_x$] + 2 H—NR$_2$, where Ni(NR$_2$)$_2$ is bis[bis(trimethylsilyl)amido]nickel(II), R is Si(Me$_3$), x is 2, 3, or 4, py is pyridine, H—OAr is an alkyl phenol, and [Ni(OAr)$_2$(py)$_x$] is a nickel(II) aryloxide.

2. The method of claim 1, wherein the alkyl phenol is a mono- or di-ortho substituted alkyl phenol.

3. The method of claim 2, wherein the mono-substituted alkyl phenol is methyl phenol (H-oMP) and the nickel(II) aryloxide is [Ni(oMP)$_2$(py)$_4$].

4. The method of claim 2, wherein the mono-substituted alkyl phenol is isopropyl phenol (H-oPP) and the nickel(II) aryloxide is [Ni(oPP)$_2$(py)$_4$].

5. The method of claim 2, wherein the mono-substituted alkyl phenol is tert-butyl phenol (H-oBP) and the nickel(II) aryloxide is [Ni(oBP)$_2$(py)$_3$].

6. The method of claim 2, wherein the di-ortho substituted alkyl phenol is di-iso-propyl phenol (H-DIP) and the nickel (II) aryloxide is [Ni(DIP)$_2$(py)$_3$].

7. The method of claim 2, wherein the di-ortho substituted alkyl phenol is di-t-butyl phenol (H-DBP) and the nickel(II) aryloxide is [Ni(DBP)$_2$(py)$_2$].

8. The method of claim 2, wherein the di-ortho substituted alkyl phenol is di-phenyl phenol (H-DPhP) and the nickel (II) aryloxide is [Ni(DPhP)$_2$(py)$_2$].

9. The method of claim 1, further comprising decomposing the nickel(II) aryloxide using a solution precipitation route to provide nickel metal nanoparticles.

10. The method of claim 9, wherein the solution precipitation route comprises dissolving the nickel (II) aryloxide in a high boiling point amine solvent to form an amine solution, and injecting the amine solution into heated hexadecylamine to generate the nickel metal nanoparticles.

11. The method of claim 10, wherein the high boiling point amine solvent comprises octylamine.

12. The method of claim 9, wherein the nickel metal nanoparticles comprise hcp Ni.

13. The method of claim 9, wherein the nickel metal nanoparticles comprise fcc Ni.

* * * * *